(12) United States Patent
Nair et al.

(10) Patent No.: US 10,696,613 B1
(45) Date of Patent: Jun. 30, 2020

(54) GAS PHASE PROCESS FOR CHLOROTRIFLUOROETHYLENE

(71) Applicant: HONEYWELL INTERNATIONAL INC., Morris Plains, NJ (US)

(72) Inventors: Haridasan K. Nair, Williamsville, NY (US); Rajiv Ratna Singh, Getzville, NY (US); Mark Makar, Buffalo, NY (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 16/506,741

(22) Filed: Jul. 9, 2019

(51) Int. Cl.
*C07C 17/25* (2006.01)
*C07C 21/18* (2006.01)

(52) U.S. Cl.
CPC .............. *C07C 17/25* (2013.01); *C07C 21/18* (2013.01); *C07C 2521/06* (2013.01)

(58) Field of Classification Search
CPC ......... C07C 17/23; C07C 21/18; C07C 17/10; C07C 21/06
See application file for complete search history.

(56) References Cited

U.S. PATENT DOCUMENTS 5,716,590 A * 2/1998 Roewer .................... A62D 3/37
423/342

FOREIGN PATENT DOCUMENTS

EP         0416615 B1 * 12/1995  ............. C07C 17/23

* cited by examiner

*Primary Examiner* — Jafar F Parsa
(74) *Attorney, Agent, or Firm* — Roberts & Roberts, LLP; Richard S. Roberts, Jr.

(57) ABSTRACT

Disclosed are processes for the dechlorination of haloethanes comprising reacting in the gaseous phase a haloethane and reducing agent such as an alkene, an alkane, hydrogen or combinations of two or more of these, in the presence of a silicon-based catalyst.

19 Claims, 1 Drawing Sheet

GAS PHASE PROCESS FOR CHLOROTRIFLUOROETHYLENE

FIELD OF THE INVENTION

The present invention relates to a gas-phase process for the preparation of 1-chloro-1,2,2-trifluoroethene (sometimes referred to herein for convenience as CTFE) by the dechlorination of 1,1,2-trichloro-1,2,2-trifluoroethane (sometimes referred to herein for convenience as CFC-113 or R-113).

BACKGROUND

CTFE is a commercially important compound, including for use as monomer in the production of fluoropolymers.

Various methods have been used to prepare CTFE. These methods have suffered from certain disadvantages including consumption of expensive materials, low product yield or both. For example, CTFE has been prepared by a liquid phase process comprising dechlorinating 1,1,2-trichloro-1,2,2-trifluoroethane with zinc in a solvent such as methanol or ethanol. See U.S. Pat. No. 5,124,494 and US 2017/0166501. Although CTFE can be produced using processes such as these, and potentially in good yield, applicants have come to appreciate that such processes have the disadvantages of requiring a large amount of solvent and producing a zinc chloride by-product which is troublesome and expensive to remove from the reaction product. U.S. Pat. No. 5,124,494 also mentions a method for producing CTFE by reacting R-113 with hydrogen in the presence of a copper, nickel or cobalt catalyst, but reports that such a process suffers from the disadvantages of low selectivity and large amounts of impurities.

CTFE has also been prepared by the co-pyrolysis of dichlorofluoromethane and chlorodifluoromethane. However, the production of CTFE by such a co-pyrolysis suffers from the disadvantage of producing CTFE in low yield.

CTFE has been prepared by the gas phase dechlorination of 1,1,2-trichloro-1,2,2-trifluoroethane with hydrogen in the presence of various active carbon catalysts. In the gas phase process using active carbon, a space velocity cannot be larger than about 500 $hr^{-1}$ resulting in low productivity. A gas phase dechlorination using a Pd catalyst has been suggested, but Pd is expensive and deactivated in a short reaction time, and the reaction carried out at a contact time of 10 to 60 seconds, so that the productivity is low. Also, the yield of CTFE was unsatisfactory.

CTFE was prepared according to a gas phase dechlorination process in U.S. Pat. No. 4,155,941. The main disadvantages of this process are reduced conversion of the starting material, low yield of the CTFE product and/or the formation of undesired material ($CF_2=CCl_2$) in significant amount (>70% in some cases with $Al_2O_3/FeCl_3$ catalyst).

There is a continuing need in the art for further improvements in processes for the production of CTFE. The present invention process produces CTFE in excellent selectivity, acceptable conversion, desirably low amounts of organic by-products and easily separated inorganic by-products.

SUMMARY OF THE INVENTION

The present invention provides processes for the dechlorination of haloethanes comprising reacting in the gaseous phase a haloethane and reducing agent, preferably selected from an alkene, an alkane, hydrogen or combinations of two or more of these, in the presence of a silicon-based catalyst. For the purposes of convenience, processes according to this paragraph are referred to herein as Process 1.

The present invention also provides processes for the dechlorination of 1,1,2-trichloro-1,2,2-trifluoroethane ($CF_2Cl—CFCl_2$; CFC-113) comprising reacting in the gaseous phase R-113 and hydrogen to produce CTFE ($CF_2=CFCl$). For the purposes of convenience, processes according to this paragraph are referred to herein as Process 2.

The processes of the present invention also include providing a gas phase mixture of 1,1,2-trichloro-1,2,2-trifluoroethane ($CF_2Cl—CFCl_2$; CFC-113) and a reducing agent, preferably selected from an alkane (such as methane, ethane, propane, isobutane, etc.), alkene (such as ethylene, propylene, butylene, etc.), or hydrogen or a combination of two or more of these in a reactor and reacting the mixture at a reaction temperature of from about 400° C. to about 600° C. in the presence of silicon-based catalyst, preferably by passing the reactant mixture over a bed of said catalyst, to produce CTFE ($CF_2=CFCl$) as the main reaction product. For the purposes of convenience, processes according to this paragraph are referred to herein as Process 3.

The processes of the present invention include providing a gas phase mixture of 1,1,2-trichloro-1,2,2-trifluoroethane ($CF_2Cl—CFCl_2$; CFC-113) and hydrogen and reacting the mixture at temperature of from about 400° C. to about 600° C. in the presence of a metal-based catalyst wherein the metal is selected from the group consisting of iron, nickel, silicon, titanium and combinations of two or more of these, preferably by passing the reactant mixture over a bed of the catalyst, to produce CTFE ($CF_2=CFCl$). For the purposes of convenience, processes according to this paragraph are referred to herein as Process 4.

The processes of the present invention include providing a gas phase mixture of 1,1,2-trichloro-1,2,2-trifluoroethane ($CF_2Cl—CFCl_2$; CFC-113) and hydrogen and reacting the mixture at temperature of from about 400° C. to about 600° C. in the presence of a, metal carbide, metal nitride, metal oxide and combinations of two or more of these, wherein the metal is selected from the group consisting of iron, nickel, silicon, titanium and combinations of two or more of these. For the purposes of convenience, processes according to this paragraph are referred to herein as Process 5

The processes of the present invention include providing a gas phase mixture of 1,1,2-trichloro-1,2,2-trifluoroethane ($CF_2Cl—CFCl_2$; CFC-113) and a reducing agent selected from an alkane (such as methane, ethane, propane, isobutane, etc.), alkene (such as ethylene, propylene, butylene, etc.), or hydrogen or a combination of two or more of these and reacting the mixture at temperature of from about 400° C. to about 600° C. in the presence of a silicon-based catalyst. For the purposes of convenience, processes according to this paragraph are referred to herein as Process 6.

The processes of the present invention include providing a gas phase mixture of 1,1,2-trichloro-1,2,2-trifluoroethane ($CF_2Cl—CFCl_2$; CFC-113) and a reducing agent selected from an alkane (such as methane, ethane, propane, isobutane, etc.), alkene (such as ethylene, propylene, butylene, etc.), hydrogen or a combination of two or more of these and reacting the mixture at temperature of from about 400° C. to about 600° C. in the presence of a silicon oxide, silicon carbide, silicon nitride and combinations of two or more of these. For the purposes of convenience, processes according to this paragraph are referred to herein as Process 7

The processes of the present invention include providing a gas phase mixture of 1,1,2-trichloro-1,2,2-trifluoroethane ($CF_2Cl—CFCl_2$; CFC-113) and hydrogen and reacting the mixture at temperature of from about 400° C. to about 600° C. in the presence of a silicon-based, preferably a silicon-carbide, catalyst. For the purposes of convenience, processes according to this paragraph are referred to herein as Process 8.

The processes of the present invention include providing a gas phase mixture of 1,1,2-trichloro-1,2,2-trifluoroethane ($CF_2Cl$—$CFCl_2$; CFC-113) and a reducing agent selected from an alkane (such as methane, ethane, propane, isobutane, etc.), alkene (such as ethylene, propylene, butylene, etc.), hydrogen or a combination of two or more of these and reacting the mixture at temperature of from about 400° C. to about 600° C. in the presence of a silicon oxide, silicon carbide, silicon nitride and combinations of two or more of these. For the purposes of convenience, processes according to this paragraph are referred to herein as Process 9.

The processes of the present invention include providing a gas phase mixture of 1,1,2-trichloro-1,2,2-trifluoroethane ($CF_2Cl$—$CFCl_2$; CFC-113) and a reducing agent selected from an alkane (such as methane, ethane, propane, isobutane, etc.), alkene (such as ethylene, propylene, butylene, etc.), or hydrogen or a combination of two or more of these and reacting the mixture at temperature of from about 400° C. to about 600° C. in the presence of a silicon-based, preferably a silicon-carbide, catalyst, wherein the molar ratio of CFC-113 to the reducing agent is from about 1:1 to about 1:10. For the purposes of convenience, processes according to this paragraph are referred to herein as Process 10.

The processes of the present invention include providing a gas phase mixture of 1,1,2-trichloro-1,2,2-trifluoroethane ($CF_2Cl$—$CFCl_2$; CFC-113) and a reducing agent selected from an alkane (such as methane, ethane, propane, isobutane, etc.), alkene (such as ethylene, propylene, butylene, etc.), hydrogen or a combination of two or more of these and reacting the mixture at temperature of from about 400° C. to about 600° C. in the presence of a silicon oxide, silicon carbide, silicon nitride and combinations of two or more of these, wherein the molar ratio of CFC-113 to the reducing agent is from about 1:1 to about 1:10. For the purposes of convenience, processes according to this paragraph are referred to herein as Process 11.

The processes of the present invention include providing a gas phase mixture of 1,1,2-trichloro-1,2,2-trifluoroethane ($CF_2Cl$—$CFCl_2$; CFC-113) and hydrogen and reacting the mixture at temperature of from about 400° C. to about 600° C. in the presence of a silicon-based, preferably a silicon-carbide, catalyst, wherein the molar ratio of CFC-113 to hydrogen is from about 1:1 to about 1:10. For the purposes of convenience, processes according to this paragraph are referred to herein as Process 12.

The processes of the present invention include providing a gas phase mixture of 1,1,2-trichloro-1,2,2-trifluoroethane ($CF_2Cl$—$CFCl_2$; CFC-113) and a reducing agent selected from an alkane (such as methane, ethane, propane, isobutane, etc.), alkene (such as ethylene, propylene, butylene, etc.), hydrogen or a combination of two or more of these and reacting the mixture at temperature of from about 400° C. to about 600° C. in the presence of a silicon oxide, silicon carbide, silicon nitride and combinations of two or more of these to produce CTFE ($CF_2$=CFCl) wherein the molar ratio of CFC-113 to the reducing agent is from about 1:1 to about 1:10. For the purposes of convenience, processes according to this paragraph are referred to herein as Process 13.

The processes of the present invention include providing a gas phase mixture of 1,1,2-trichloro-1,2,2-trifluoroethane ($CF_2Cl$—$CFCl_2$; CFC-113) and a reducing agent selected from an alkane (such as methane, ethane, propane, isobutane, etc.), alkene (such as ethylene, propylene, butylene, etc.), hydrogen or a combination of two or more of these and reacting the mixture at temperature of from about 400° C. to about 600° C. in the presence of a silicon-based, preferably a silicon-carbide, catalyst, wherein the molar ratio of CFC-113 to the reducing agent is from about 1:1 to about 1:3. For the purposes of convenience, processes according to this paragraph are referred to herein as Process 14.

The processes of the present invention include providing a gas phase mixture of 1,1,2-trichloro-1,2,2-trifluoroethane ($CF_2Cl$—$CFCl_2$; CFC-113) and a reducing agent selected from an alkane (such as methane, ethane, propane, isobutane, etc.), alkene (such as ethylene, propylene, butylene, etc.), hydrogen or a combination of two or more of these and reacting the mixture at temperature of from about 400° C. to about 600° C. in the presence of a silicon oxide, silicon carbide, silicon nitride and combinations of two or more of these, wherein the molar ratio of CFC-113 to the reducing agent is from about 1:1 to about 1:3. For the purposes of convenience, processes according to this paragraph are referred to herein as Process 15.

The processes of the present invention include providing a gas phase mixture of 1,1,2-trichloro-1,2,2-trifluoroethane ($CF_2Cl$—$CFCl_2$; CFC-113) and hydrogen and reacting the mixture at a temperature of from about 400° C. to about 600° C. in the presence of a silicon-based, preferably a silicon-carbide, catalyst, wherein the molar ratio of CFC-113 to hydrogen is from about 1:1 to about 1:3. For the purposes of convenience, processes according to this paragraph are referred to herein as Process 16.

The processes of the present invention include providing a gas phase mixture of 1,1,2-trichloro-1,2,2-trifluoroethane ($CF_2Cl$—$CFCl_2$; CFC-113) and a reducing agent selected from an alkane (such as methane, ethane, propane, isobutane, etc.), alkene (such as ethylene, propylene, butylene, etc.), hydrogen or a combination of two or more of these and reacting the mixture at temperature of from about 400° C. to about 600° C. in the presence of a silicon oxide, silicon carbide, silicon nitride and combinations of two or more of these to produce CTFE ($CF_2$=CFCl), wherein the molar ratio of CFC-113 to the reducing agent is from about 1:1 to about 1:3. For the purposes of convenience, processes according to this paragraph are referred to herein as Process 17.

The processes of the present invention include providing a gas phase mixture of 1,1,2-trichloro-1,2,2-trifluoroethane ($CF_2Cl$—$CFCl_2$; CFC-113) and a reducing agent selected from an alkane (such as methane, ethane, propane, isobutane, etc.), alkene (such as ethylene, propylene, butylene, etc.), or hydrogen or a combination of two or more of these and reacting the mixture at temperature of from about 400° C. to about 600° C. in the presence of a silicon-based, preferably a silicon-carbide catalyst to produce a reaction product comprising CTFE, wherein the selectivity to CTFE is 95% or greater. For the purposes of convenience, processes according to this paragraph are referred to herein as Process 18.

The processes of the present invention include providing a gas phase mixture of 1,1,2-trichloro-1,2,2-trifluoroethane ($CF_2Cl$—$CFCl_2$; CFC-113) and a reducing agent selected from an alkane (such as methane, ethane, propane, isobutane, etc.), alkene (such as ethylene, propylene, butylene, etc.), hydrogen or a combination of two or more of these and reacting the mixture at temperature of from about 400° C. to about 600° C. in the presence of a silicon oxide, silicon carbide, silicon nitride and combinations of two or more of these to produce a reaction product comprising CTFE, wherein the selectivity to CTFE is 95% or greater. For the purposes of convenience, processes according to this paragraph are referred to herein as Process 19.

The processes of the present invention include providing a gas phase mixture of 1,1,2-trichloro-1,2,2-trifluoroethane ($CF_2Cl$—$CFCl_2$; CFC-113) and hydrogen and reacting the mixture at temperature of from about 400° C. to about 600° C. in the presence of a silicon-based, preferably a silicon-carbide, catalyst, to produce a reaction product comprising CTFE, wherein the selectivity to CTFE is 95% or greater. For the purposes of convenience, processes according to this paragraph are referred to herein as Process 20.

The processes of the present invention include providing a gas phase mixture of 1,1,2-trichloro-1,2,2-trifluoroethane ($CF_2Cl$—$CFCl_2$; CFC-113) and a reducing agent selected from an alkane (such as methane, ethane, propane, isobutane, etc.), hydrogen or a combination of two or more of these and reacting the mixture at temperature of from about 400° C. to about 600° C. in the presence of a silicon oxide, silicon carbide, silicon nitride and combinations of two or more of these to produce a reaction product comprising CTFE, wherein the selectivity to CTFE is 95% or greater. For the purposes of convenience, processes according to this paragraph are referred to herein as Process 21.

The present invention also provides processes for the dechlorination of haloethanes comprising reacting in the gaseous phase a haloethane and reducing agent, preferably selected from an alkene, an alkane, hydrogen or combinations of two or more of these, in the presence of a silicon-based catalyst to produce a reaction product that is substantially free of each of $CH_3Cl$, $CF_2(CH_3)_2$, $CF_2$=$CHCl$, $F_2ClCCCl_2H$ (123a) and $CF_2$=$CCl_2$ and which has a CTFE selectivity of at least about 96% and a conversion of at least about 15%. For the purposes of convenience, processes according to this paragraph are referred to herein as Process 22.

The present invention also provides processes for the dechlorination of 1,1,2-trichloro-1,2,2-trifluoroethane ($CF_2Cl$—$CFCl_2$; CFC-113) comprising reacting in the gaseous phase R-113 and hydrogen to produce a reaction product that is substantially free of each of $CH_3Cl$, $CF_2(CH_3)_2$, $CF_2$=$CHCl$, $F_2ClCCCl_2H$ (123a) and $CF_2$=$CCl_2$ and which has a CTFE selectivity of at least about 96% and a conversion of at least about 25% CTFE ($CF_2$=$CFCl$). For the purposes of convenience, processes according to this paragraph are referred to herein as Process 23.

DETAILED DESCRIPTION

The present invention provides a process for producing a haloethylene, and particularly perhaloethylenes, by the dechlorination of the haloethane comprising reacting in the gaseous phase the haloethane and a reducing agent, such as an alkene, an alkane, hydrogen or combinations of these in the presence of a catalyst. The preferred gas phase process of the present invention involve the vicinal dechlorination of the haloethane in the presence of the catalyst to provide a haloethylene. In preferred aspects, the reducing agent is used in the gas phase reaction to react with the chlorine produced by the dechlorination.

Definitions:

The term "conversion" with respect to a reactant refers to the mole percentage of that particular reactant which is converted to another compound in the reaction.

The term "selectivity" with respect to a desired reaction product refers to the moles of desired produced by the reaction as a percentage of all reaction products (exclusive of unreacted feed and amounts recycled).

The term "contact time" means the theoretical mean residence time and is calculated by dividing the reactor free space by the volumetric reactor flow rate. Thus, contact time in minutes is calculated by dividing the volume of the heated catalyst bed in the reactor (or its equivalent in the case of reactor without catalyst) divided by the standard cubic centimeters per minute (SSCM) of feed to the reactor.

The term "reaction temperature" refers to the mean temperature of the reactants in the reactor.

As used herein, the terms "silicon-based catalyst," "silicon carbide catalyst," "silicon nitride catalyst," silicon oxide catalyst" and the like are used in the broad sense to reflect that the indicated material is present during the reaction, but does not participate as a reactant in the reaction of the present invention, and when present serves to improve one or more of conversion, selectivity, by-product reduction or other reaction parameter compared to the same process without the indicated material.

The term "substantially free" refers an amount that produces a molar concentration in the reaction product of not greater than 1%.

Preferred Haloethane Reactants

In preferred embodiments the haloethane starting material has at least one chlorine one each of the carbon atoms, which are eliminated during the gas-phase dechlorination process.

The preferred haloethane starting material is R-113 and the preferred reaction product is CTFE, and the net reaction proceeds according to the following reaction scheme when the reducing agent is hydrogen and a catalyst is present:

$$F_2ClC\text{—}CCl_2F + H_2 \xrightarrow{\text{Dechlorination catalyst}} F_2C\text{=}CFCl + 2HCl$$

According to preferred embodiments, the haloethane reactant is a perhaloethane having at least one chlorine atom on each of the carbons, with remaining substituents being fluorine atoms.

Preferred perhaloethanes include 1,2-dichlorotetrafluoroethane (fluorocarbon 114) and 1,1,2-trichloro-1,2,2-trifluoroethane (R-113), with 1,1,2-trichloro-1,2,2-trifluoroethane being particularly preferred. When two chlorines are removed from these preferred halohydrocarbons, the products are perhaloethylenes including, for example, tetrafluoroethylene or CTFE.

Reducing Agents

The processes of the present invention include as part of the the gas phase reaction mixture a reducing agent which serves to react with the chlorine ($Cl_2$) and/or chlorine radical that is formed by the dechlorination reaction. For the purposes of convenience, the reducing agent is sometimes also referred to herein as a chlorine scavenger. The chlorine scavenger preferably is an alkane, an alkene, or hydrogen that reacts with chlorine generated during the dechlorination reaction and thus produces a reaction product that does not include any substantial chlorine gas.

Applicants have found that substantial advantages can be achieved using hydrogen as the reducing agent according to the present invention, and accordingly it is preferred that the processes of the present invention, including each of Processes 1-23, use hydrogen as a reducing agent. In particular, applicants have found that the main by-product of the reduction reaction involving hydrogen is HCl, which is relatively easily removed from the reaction product mixture compared to the by-products that are frequently produced using other reducing agents. In addition, applicants have found that the use of hydrogen permits the overall reaction to proceed with very high levels of selectivity to CTFE. For this reason, the present processes, including each of Processes 1-23, include the use of a reducing agent that comprises, or consists essentially of, or consists of hydrogen.

When used, preferred alkanes have 1 to 6 carbon atoms, and more preferably 1 to 4 carbon atoms. Alkanes for use as chlorine scavengers in the dechlorination reaction include methane, ethane, propane, butane, isobutane, pentane, hexane, and the like, and particularly methane, ethane, propane and isobutane, most particularly propane. Alternatively, the alkane may be a cycloalkane such as cyclopentane and cyclohexane.

Preferred alkenes have from 2 to 6 carbon atoms, and more preferably 2 or 3 carbon atoms.

When used, preferred alkenes for use as chlorine scavengers in the dechlorination reaction include ethylene, propylene, butylene, pentene, and the like. Alternatively, the alkene may be a cycloalkene such as cyclopentene and cyclohexene.

The molar ratio of the haloethane starting material (e.g, CFC-113) to the reducing agent according to the present invention, including each of Process 1-23, is preferably between about 1:1 to about 1:10. The molar ratio of the haloethane starting material (e.g., CFC-113) to the reducing agent according to the present invention, including each of Process 1-23, is preferably between about 1:1 to about 1:3.

Preferred Perhaloethane Reaction Product Streams

The processes of the present invention, including each of Processes 1-23, produce a reaction product stream that comprises CTFE and unreacted haloethane reactants. In preferred embodiments, at least a portion, and preferably a substantial portion, and preferably substantially of the unreacted haloethane (such as R-113) is separated from the reaction product stream and recycled to the reaction step.

The processes of the present invention, including each of Processes 1-23, also preferably produce a reaction product stream that comprises CTFE and unreacted haloethane reactants, including particularly unreacted R-113, but which is substantially free of at least one of $CH_3Cl$, $CF_2(CH_3)_2$, $CF_2=CHCl$, $CF_2=CFH$, $F_2ClC-CCl_2H$ (123a) and $CF_2=CCl_2$.

The processes of the present invention, including each of Processes 1-23, also preferably produce a reaction product stream that comprises CTFE and unreacted haloethane reactants, including particularly unreacted R-113, but which is substantially free of at least one of $CH_3Cl$, $CF_2(CH_3)_2$, $CF_2=CHCl$, $CF_2=CFH$, $F_2ClC-CCl_2H$ (123a) and $CF_2=CCl_2$.

The processes of the present invention, including each of Processes 1-23, also preferably produce a reaction product stream that comprises CTFE and unreacted haloethane reactants, including particularly unreacted R-113, but which is substantially free of at least one of $CH_3Cl$, $CF_2(CH_3)_2$, $CF_2=CHCl$, $CF_2=CFH$, $F_2ClC-CCl_2H$ (123a) and $CF_2=CCl_2$.

The processes of the present invention, including each of Processes 1-23, also preferably produce a reaction product stream that comprises CTFE and unreacted haloethane reactants, including particularly unreacted R-113, but which contains less than 500 ppm (molar) of at least one of $CH_3Cl$, $CF_2(CH_3)_2$, $CF_2=CHCl$, $CF_2=CFH$, $F_2ClC-CCl_2H$ (123a) and $CF_2=CCl_2$.

The processes of the present invention, including each of Processes 1-23, also preferably produce a reaction product stream that comprises CTFE and unreacted haloethane reactants, including particularly unreacted R-113, but which is substantially free of each of $CH_3Cl$, $CF_2(CH_3)_2$, $CF_2=CHCl$, $CF_2=CFH$, $F_2ClC-CCl_2H$ (123a) and $CF_2=CCl_2$.

The processes of the present invention, including each of Processes 1-23, also preferably produce a reaction product stream that comprises CTFE and unreacted haloethane reactants, including particularly unreacted R-113, but which contains less than 500 ppm (molar) of each of $CH_3Cl$, $CF_2(CH_3)_2$, $CF_2=CHCl$, $CF_2=CFH$, $F_2ClC-CCl_2H$ (123a) and $CF_2=CCl_2$.

Catalysts

The catalyst materials that may be used in accordance with the present invention, including particularly Processes 2, 4, 5, 8, 12, 16, 20 and 22 include metal oxides, metal chlorides, metal fluorides, metal carbides, metal nitrides and combinations of these. In certain preferred embodiments, the metal of the metal-based catalyst in accordance with the present invention, including particularly each of Processes 2, 4, 5, 8, 12, 16, 20 and 22, is selected from transition metals of a group 8, group 9, or group 10, silicon, and combinations of two or more of these. When present, the transition metal of the catalyst may be selected from Fe, Ru, Co, Rh, Ni, Pd, Pt, Cu and Ag.

The preferred catalyst materials in accordance with the present invention, including particularly each of Processes 2, 4, 5, 8, 12, 16, 20 and 22 include metal oxides, such as silicon oxide, iron (III) oxide, nickel (II) oxide, copper (II) oxide, and combinations of any two or more thereof. They also include transition metals such as copper (II), iron (III) and iron (III).

Preferred among the iron compounds in accordance with the present invention, including particularly each of Processes 2, 4, 5, 8, 12, 16, 20 and 22, are iron at valence state 3, including iron (II) and iron (III) oxide.

Preferred among the nickel compounds in accordance with the present invention, including each of particularly Processes 2, 4, 5, 8, 12, 16, 20 and 22 are nickel at valence state 2, including nickel (II) compounds, such as including NiO.

Preferred among the copper compounds in accordance with the present invention, including particularly each of Processes 2, 4, 5, 8, 12, 16, 20 and 22, are copper at valence state 2, including CuO, $CuF_2$ and $CuCl_2$.

According to preferred embodiments of the present invention, including particularly each of Processes 1-23 the dechlorination catalyst comprises, consists essentially of, or consists of silicon and/or a nitride, carbide or oxide of silicon. Among the silicon-based catalysts, silicon carbide and silicon nitride are preferred. As used herein, the term silicon carbide refers to all compounds consisting of silicon and carbon. Preferred silicon carbide (carborundum) is available from several sources, including under the trade designation Carborex® by Washington Mills or Advanced Ceramics-Materials GmbH, Germany As used herein, the term silicon nitride refers to all compounds consisting of silicon and nitrogen. Preferred among the silicon nitrides is $Si_3N_4$. Preferred silicon nitride is available from several sources, including from UBE Industries, LTD.

According to preferred embodiments of the present invention, including each of Processes 1-23 the dechlorination catalyst comprises, consists essentially of, or consists of silicon carbide.

According to preferred embodiments of the present invention, including each of Processes 1-23 the dechlorination catalyst comprises, consists essentially of, or consists of silicon nitride.

According to preferred embodiments of the present invention, including each of Processes 1-23 the dechlorination catalyst comprises, consists essentially of, or consists of silicon oxide.

Applicants have found that the use of silicon-based catalyst provides several important and unexpected advantages according to the processes of the present invention, including each of Processes 1-23. In particular, the silicon carbide catalyst is extremely robust and thermally stable while at the same time providing very high levels of selectivity to CFTE. As a result, the preferred processes of the present invention which use silicon carbide catalyst provide relatively long run-times, that is, run times that are long relative to other catalysts. In addition, the preferred processes of the present invention which use silicon carbide catalyst require relatively infrequent regeneration, and possibly no regeneration, to maintain high catalyst activity.

In processes of the present invention, including each of Processes 1-23, the catalyst may be used without a support or on a support. When used in processes of the present invention, including each of Processes 1-23, supports preferably include carbon, which may either pellet or granular type which are commercially available. In processes of the present invention, including each of Processes 1-23, catalyst loading on the support (for those embodiments in which a support is used) may be from about 2% to about 25%, or from about 5% to about 20% on the support. Applicants have found that the preferred silicon-based catalysts of the present invention, including particularly silicon carbides, silicon nitrides and silicon oxides, have the unexpected advantage of being extraordinarily robust in use, and this robust character is present even in cases where the catalyst is unsupported. Accordingly, the present invention includes processes, including each of Processes 1-23, in which the silicon-based catalyst is used in an unsupported form, including unsupported silicon carbide, unsupported silicon nitride and unsupported silicon oxide.

In processes of the present invention, including each of Processes 1-23, the catalyst can comprise silicon carbide supported on carbon, silicon nitride supported on carbon, and/or silicon oxide supported on carbon.

To the extend and when regeneration of the catalyst is desired or wanted, the catalyst may be optionally regenerated in situ. Regeneration of the catalyst may be accomplished by passing an oxidizing agent over the catalyst, for example, by passing air or oxygen, optionally diluted with nitrogen, over the catalyst. Regeneration may be performed at temperatures of from about 400° C. to about 650° C., preferably from about 500° C. to about 625° C., and for about 4 hours to about 48 hours, depending on the size of the reactor.

In preferred embodiments, the processes of the present invention, including each of Processes 1-23, proceed for an extended reaction run without regeneration of the catalysts and with no or only minimal reduction in the conversion of the haloethane reactant. In preferred embodiments, the processes of the present invention, including each of Processes 1-23, proceed for an extended reaction run without regeneration of the catalysts and with no or only minimal reduction in the conversion of the haloethane reactant and no or minimal reduction of the selectivity to CTFE. As used herein, the term minimal reduction with respect to conversion means that once steady state conversion is reached, the conversion does not decrease from the average steady state value by more than about 10% (relative) for an extended reaction run, for example, for reaction run time of 5 hours, or for 6 hours, or for more than 6 hours. As used herein, the term minimal reduction with respect to selectivity means that selectivity is not reduced by more than 1% compared to the initial selectivity. As used herein, the term "extended reaction run" means that the reaction proceeds for at least five (5) hours without regeneration or treatment of the catalyst.

Process Configuration and Conditions

Figure 1:
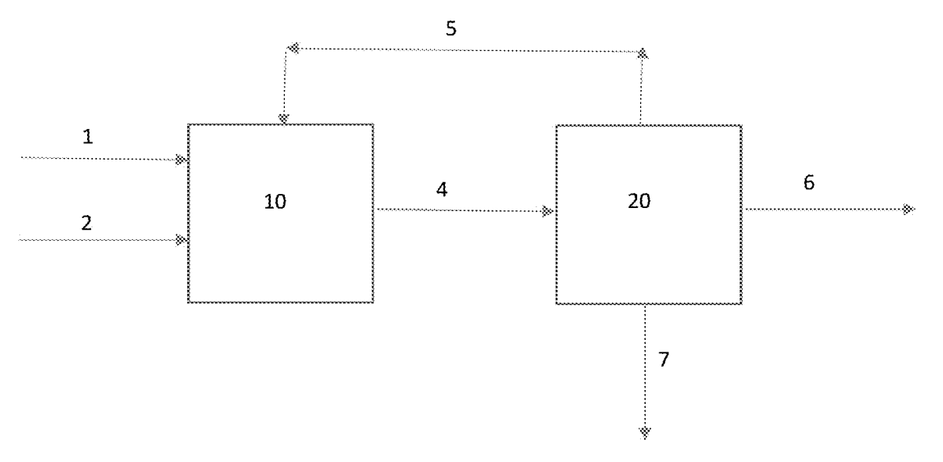

A generalized process flow diagram illustrating the preferred processes according to the present invention is provided in FIG. 1. Generally, the preferred processes include a reactor 10 which receives a haloethane reactant stream 1 and a reducing agent stream 2. It will be appreciated by those skilled in the art that although streams one and two are shown as being separately fed to the reactor, it is possible and may be desirable in some embodiments, including each of Processes 1-23, for the contents of those feed streams to be combined in advance of the reactor and introduced to the reactor as a single feed stream. Both such embodiments are within the scope of the present invention. Preferably, the reactor according to the present invention, including each of Processes 1-23, is capable of receiving one or more recycle streams 5, as explained in more detail hereinafter. The reaction product 4 exits the reactor and preferably including in each of Processes 1-23, is introduced to a separation stage 20 in which a relatively pure desired reaction product stream 6 and one or more byproduct streams 7 are produced.

As described above, the reaction product stream 4 may include some portion of the unreacted feed streams 1 and 2, and in preferred embodiments, including each of Processes 1-23, a proportion of such unreacted feed streams (and preferably in many embodiments, including each of Processes 1-23, substantially all of the unreacted feed) is separated from the reaction product and returned to the reactor 10 via recycle stream 5. It will be appreciated, however, that depending on the needs of any particular operation it may be possible to eliminate the recycle stream 5 and to allow unreacted feed components to be included in product stream 6 and/or by-product stream 7.

The reaction of the present invention, including each of Processes 1-23, may be conducted batch-wise, continuous or a combination of batch and continuous, although a continuous reactor is generally preferred. In preferred embodiments, including each of Processes 1-23, the reactor comprises a tubular, continuous reactor which contains the catalyst in solid form, either as a packed bed or otherwise, and has an internal heat source and/or an external heat source to maintain the reaction temperature within preferred reaction temperature ranges. According to the present invention, including each of Processes 1-23, the reactor itself may be single or multiple stages and can take any form of any reactor suitable for a vapor phase dechlorination reaction. Preferably according to the present invention, including each of Processes 1-23, the reactor is constructed from materials that are resistant to the corrosive effects of chlorine, catalyst, or byproducts, such as stainless steel, Hastelloy, Inconel, Monel.

Optionally, an inert diluent may be used with the dechlorination reaction. The inert diluent is any material that is in the vapor phase under the reaction conditions and is nonreactive to any of the components present in the reactor during the dechlorination reaction. The inert diluent may include nitrogen or the like.

According to the present invention, including each of Processes 1-23, the temperature range for the dechlorination reaction may vary depending on the combination of catalyst, haloethane starting material and reducing agent. In order to have the dechlorination reaction occur in the gaseous phase, the temperature and pressure according to the present invention, including each of Processes 1-23, should be such that all reactants are in the vapor phase. Also, according to the present invention, including each of Processes 1-23, temperatures at or above the decomposition temperatures of reactants and products should be avoided.

Preferred dechlorination reaction temperatures according to the present invention, including each of Processes 1-23, are from about 400° C. to about 650° C., more preferably from about 450° C. to about 600° C., and even more preferably from about 500° C. and about 600° C. The temperature for the gas-phase dechlorination reaction according to the present invention, including each of Processes 1-23, may be above 500° C., or above about 550° C. and up to about 600° C.

The contact time in the reactor according to the present invention can vary depending on the particular needs of a particular application. Generally, for preferred embodiments in which the reaction temperature is from about 400 to about 650 C, the reactor is configured according to the present invention, including each of Processes 1-23, to have a contact time of about 1 to about 6 seconds, more preferably of from about 3 to about 5 seconds. In addition, for preferred embodiments in which the reaction temperature is from about 400 to about 650 C, the reactor is configured according to the present invention, including each of Processes 1-23, to have a contact time of about 1 to about 6 seconds, more preferably of from about 3 to about 5 seconds.

In preferred embodiments according to the present invention, including each of Processes 1-23, the reaction step utilizes a combination of reaction temperature, contact times, catalyst type and reactant ratios to produce a selectivity to the desired haloalkane product, and preferably CTFE, that is at least 80%.

In preferred embodiments according to the present invention, including each of Processes 1-23, the reaction step utilizes a combination of reaction temperature, contact times, catalyst type and reactant ratios to produce a selectivity to the desired haloalkane product, and preferably CTFE, that is at least 90%.

In preferred embodiments according to the present invention, including each of Processes 1-23, the reaction step utilizes a combination of reaction temperature, contact times, catalyst type and reactant ratios to produce a selectivity to the desired haloalkane product, and preferably CTFE, that is at least about 95%.

In preferred embodiments according to the present invention, including each of Processes 1-23, the reaction step utilizes a combination of reaction temperature, contact times, catalyst type and reactant ratios to produce a selectivity to the desired haloalkane product, and preferably CTFE, that is at least about 96%.

In preferred embodiments, the reaction step of the present invention including each of Processes 1-23, utilizes a combination of reaction temperature, contact times, catalyst type and reactant ratios to produce a total halocarbon by-product and hydrohalocarbon by-product yield that is less than 2%, more preferably less than 1.5%, and even more preferably less than 1%.

The conversion of the starting haloalkane by the process of the present invention can vary widely. In general, conversion according to the present invention, including each of Processes 1-23, is preferably from about 10% to about 95%.

In preferred embodiments in which the reducing agent comprises, consists essentially of or consists of hydrogen and the catalyst comprises, consists essentially of or consists of silicon-based catalyst, according to the present invention, including each of Processes 1-23, the conversion is preferably from about 15% to about 60%.

In preferred embodiments in which the reducing agent comprises, consists essentially of or consists of hydrogen and the catalyst comprises, consists essentially of or consists of silicon-based catalyst, according to the present invention, including each of Processes 1-23, the conversion is preferably from about 15% to about 50%.

In preferred embodiments in which the reducing agent comprises, consists essentially of or consists of hydrogen and the catalyst comprises, consists essentially of or consists of silicon-based catalyst, according to the present invention, including each of Processes 1-23, the conversion is preferably from about 15% to about 50% and the selectivity to CTFE is at least about 95%.

The following non-limiting examples serve to illustrate certain embodiments of the invention but are not to be construed as limiting. Variations and additional or alternative embodiments will be readily apparent to the skilled artisan on the basis of the disclosure provided herein.

In the Examples and the Comparative Examples, the conversion and selectivity are the values calculated as follows:

$$\text{Conversion of } R113(\%) = 100 * ((R\text{-}113_F - R\text{-}113_U)/R113_F)$$

where $R113_F$ is the moles of raw R113 in the reactor feed $R113_U$ is the unreacted moles, with "raw" R113 referring to R113 fed to the reactor but not including any recycled R113.

Selectivity to CTFE=CTFE produced/All reaction products (exclusive of unreacted feed and amounts recycled) (all amounts in moles)

EXAMPLES

For each example, a stainless steel or Monel tubular gas-phase reactor having an inside diameter of ~0.5 inch and 8 foot of length is used. The tubular reactor is provided with a 16 cm$^3$ heating zone. For each example, the indicated catalyst was packed as a 10.8 cm$^3$ bed into the reactor. A mixture of $CF_2Cl$—$CFCl_2$ (R-113) and one of hydrogen, methane or propane in the indicated molar ratio were fed to the heated reactor. The contact times (CTs) used were in the range of 3-5 seconds.

The exit gases from the reactor were passed through water (20 mL) and a drying column (CaCl$_2$, Drierite), and collected in a Tedlar® gas bag or small metal container for analysis by GC/GC-MS.

Example 1—Gas Phase Dechlorination of
$CF_2Cl$—$CFCl_2$ to CTFE with Hydrogen and Silicon Carbide Catalyst Experiments were conducted using the process as described above in general with silicon carbide catalyst, hydrogen reducing agent and the process conditions as described in Table 1 below. The results are reported in Table 1 below:

TABLE 1

| Ex. No. | Cat. | Temp, OC | CT, sec | Ratio 113/H2 | Conv., % 113 | Sel., % CTFE | By-products, mol % CF2=CFH | 123a* |
|---|---|---|---|---|---|---|---|---|
| 1A | SiC | 450 | 3 | 1:1 | 6.7 | 96.3 | 0.2 | 0.04 |
| 1B | SiC | 500 | 3 | 1:1 | 25 | 95.8 | 1.1 | 0.14 |
| 1C | SiC | 515 | 3 | 1:1 | 25.6 | 97.3 | 0.5 | 0.2 |
| 1D1 | SiC | 525 | 3 | 1:1 | 30.6 | 96.0 | 1.1 | 0.2 |
| 1D2 | SiC | 525 | 3 | 1:1 | 25 | 95.8 | 1.2 | 0.27 |
| 1E | SiC | 525 | 1.5 | 1:1 | 24.8 | 96.8 | 0.8 | 0.18 |
| 1F | SiC | 525 | 1 | 1:1 | 18.5 | 97.3 | 0.4 | 0.1 |
| 1G | SiC | 525 | 5 | 1:1 | 31.5 | 96.0 | 0.9 | 0.4 |
| 1E | SiC | 535 | 3 | 1:1 | 29.6 | 96.5 | 0.7 | 0.3 |

*123a is 1,2-dichloro-1,1,2-trifluoroethane

As can be seen from the results reported above, processes of the present invention are capable of producing reaction product with a very high selectivity (about 96% or above in all cases tested), low by product production, and no measured production of the highly undesirable by products $CH_3Cl$, $CF_2(CH_3)_2$, or $CF_2$=CHCl. Furthermore, the conversion rates, which are all above 15% in the cases where the reaction temperature is 500° C. or greater, and as high as 31.5%, are acceptable for processes of the present invention, particularly and especially for preferred processes which utilize recycle of unconverted R-113 as described above.

Example 2—Gas Phase Dechlorination of $CF_2Cl$—$CFCl_2$ to CTFE with Silicon Carbide Catalyst and No Reducing Agent Experiments were conducted using the process as described above in general with silicon carbide catalyst, no reducing agent and the process conditions as described in Table 2 below. The results are reported in Table 2 below:

TABLE 2

| Ex. No. | Cat. | Temp, C. | CT, sec | No reducing agent | Conv % 113 | Conv., Sel. CTFE | By-products, mol % CF2=CFH | 123a* | CF2=CCl2 |
|---|---|---|---|---|---|---|---|---|---|
| 2A | SiC | 525 | 3 | | 11.1 | 97 | | | 0.2 |
| 2B | SiC | 600 | 3 | | 28.6 | 87 | | | 2.8 |
| 2C | SiC | 525 | 5 | | 8.7 | 86 | | | 1.1 |
| 2D | SiC | 535 | 3 | | 7.9 | 88.8 | | | 1 |

*123a is 1,2-dichloro-1,1,2-trifluoroethane

As can be seen from the results reported above, processes of the present invention in which no reducing agent is used are capable of producing reaction product with high selectivity (86% or above in all cases tested) and conversion rates all above about 8%, and as high as 28.6%, which are acceptable for processes of the present invention, particularly and especially for preferred processes which utilize recycle of unconverted 113 as described above. However, the process does produce the undesirable by product $CF_2$=$CCl_2$, which is not a preferred result for some applications.

Example 3—Gas Phase Dechlorination of $CF_2Cl$—$CFCl_2$ to CTFE with No Hydrogen and TiSiC Catalyst Experiments were conducted using the process of the present invention as described above, with material comprising a combination of titanium and silicon carbide as catalyst (herein referred to for convenience as TiSiC), hydrogen reducing agent and the process conditions as described in Table 3 below. The results are reported in Table 3 below:

TABLE 3

| Ex. No. | Cat. | Temp, C. | CT, sec | Ratio 113/H2 | Conv., % 113 | Sel., % CTFE | By-products, mol % $CF_2$=CFH | 123a* | $CF_2$=$CCl_2$ |
|---|---|---|---|---|---|---|---|---|---|
| 3A | TiSiC | 475 | 3 | 1:1 | 48.4 | 94.5 | 0.2 | 0.24 | 2.2 |
| 3B | TiSiC | 490 | 3 | 1:1 | 27.3 | 94.2 | 0.65 | 0.12 | 0.8 |
| 3C1 | TiSiC | 500 | 3 | 1:1 | 65.3 | 95.7 | 0.3 | 0.3 | 2.2 |
| 3C2 | TiSiC | 500 | 3 | 1:1 | 36.2 | 93.6 | 0.64 | 0.21 | 1.47 |
| 3D | TiSiC | 500 | 5 | 1:1 | 36.8 | 92.8 | 0.91 | 0.23 | 1.51 |
| 3E | TiSiC | 500 | 1 | 1:1 | 22.5 | 96.1 | 0.54 | 0.05 | 0.29 |
| 3F | TiSiC | 510 | 3 | 1:1 | 28.8 | 94.3 | 0.8 | 0.14 | 0.7 |

*123a is 1,2-dichloro-1,1,2-trifluoroethane

As can be seen from the results reported above, processes of the present invention are capable of producing reaction product with a very high selectivity (about 92% or above in all cases tested), low by-product production, and no measured production of the highly undesirable by products $CH_3Cl$, $CF_2(CH_3)_2$, or $CF_2=CHCl$. Furthermore, the conversion rates, which are all above 22%, and as high as 65.3%, are acceptable for processes of the present invention, particularly and especially for preferred processes which utilize recycle of unconverted 113 as described above.

Example 4—Gas Phase Dechlorination of $CF_2Cl$—$CFCl_2$ to CTFE with No Reducing Agent and TiSiC Catalyst Experiments were conducted using the process as described above in general with TiSiC catalyst, hydrogen reducing agent and the process conditions as described in Table 4 below. The results are reported in Table 4 below:

TABLE 4

| Ex. No. | Cat. | Temp, C. | CT, sec | No reducing agent | Conv., % 113 | Sel., % CTFE | By-products, mol % | |
|---|---|---|---|---|---|---|---|---|
| | | | | | | | $CF_2=CFH$ | $CF_2=CCl_2$ |
| 4 | TiSiC | 500 | 3 | NA | 47.3 | 95.8 | | 1.98 |

*123a is 1,2-dichloro-1,1,2-trifluoroethane

As can be seen from the results reported above, processes of the present invention in which no reducing agent is used are capable of producing reaction product with high selectivity and conversion. However, the process does produce the undesirable by product $CF_2=CCl_2$, which is not a preferred result for some applications.

Example 5—Gas Phase Dechlorination of $CF_2Cl$—$CFCl_2$ to CTFE with Hydrogen and 316 Packing as Catalyst An experiment was conducted using the process as described above in general with 316 SS packing and hydrogen reducing agent and the process conditions as described in Table 5 below. The results are reported in Table 5 below:

TABLE 5

| Ex. No. | Cat. | Temp, C. | CT, sec | Ratio 113/H2 | Conv., % 113 | Sel., % CTFE | By-products, mol % | | |
|---|---|---|---|---|---|---|---|---|---|
| | | | | | | | $CF_2=CFH$ | 123a* | $CF_2=CCl_2$ |
| 5 | 316 | 600 | 3 | 1:1 | 41.4 | 71.5 | | | |

Even though the process of this example has a desirable by-product profile, the selectivity is less than is desired for some applications.

Example 6—Gas Phase Dechlorination of $CF_2Cl—CFCl_2$ to CTFE with Hydrogen and Monel as Catalyst An experiment was conducted using the process as described above in general with Monel packing and hydrogen reducing agent and the process conditions as described in Table 6 below. The results are reported in Table 6 below:

TABLE 6

| Ex. No. | Cat. | Temp, C. | CT, sec | Ratio 113/H2 | Conv., % 113 | Sel., % CTFE | By-products, mol % | | | |
|---|---|---|---|---|---|---|---|---|---|---|
| | | | | | | | $CF_2=CFH$ | 123a* | $CF_2=CCl_2$ | |
| 5 | Monel | 480 | 3 | 1:1 | 20.4 | 77.5 | | | | |

Even though the process of this example has a desirable by-product profile, the selectivity is less than is desired for some applications.

Example 7—Gas Phase Dechlorination of $CF_2Cl—CFCl_2$ to CTFE with Hydrogen and Monel as Catalyst An experiment was conducted using the process as described above in general with Monel packing and hydrogen reducing agent and the process conditions as described in Table 7 below. The results are reported in Table 7 below:

TABLE 7

| Ex. No. | Cat. | Temp, O C. | CT, sec | Ratio 113/H2 | Conv., % 113 | Sel., % CTFE | By-products, mol % | | | |
|---|---|---|---|---|---|---|---|---|---|---|
| | | | | | | | $CF_2=CFH$ | 123a* | $CF_2=CCl_2$ | |
| 5 | Monel | 480 | 3 | 1:1 | 20.4 | 77.5 | | | | |

Even though the process of this example has a desirable by-product profile, the selectivity is less than is desired for some applications.

Example 8—Gas Phase Dechlorination of $CF_2Cl—CFCl_2$ to CTFE with Hydrogen and Nickel as Catalyst An experiment was conducted using the process as described above in general with nickel packing as catalyst and hydrogen reducing agent and the process conditions as described in Table 8 below. The results are reported in Table 8 below:

TABLE 8

| Ex. No. | Cat. | Temp, C. | CT, sec | Ratio 113/H2 | Conv., % 113 | Sel., % CTFE | By-products, mol % | | |
|---|---|---|---|---|---|---|---|---|---|
| | | | | | | | $CF_2=CFH$ | 123a* | $CF_2=CCl_2$ |
| 7A | Nickel | 500 | 1 | 1:1 | 12.2 | 94.4 | 0.7 | | |
| 7B | Nickel | 500 | 3 | 1:1 | 20.4 | 89.0 | 2.2 | 0.1 | |
| 7C | Nickel | 525 | 3 | 1:1 | 29.6 | 83.3 | 4.6 | 0.3 | |
| 7D | Nickel | 550 | 3 | 1:1 | 31.4 | 82.1 | 5.3 | 0.3 | |
| 7E | Nickel | 500 | 3 | 3:1 | 23.6 | 92.5 | 1.7 | | |

As can be seen from the results reported above, processes of the present invention are capable of producing reaction product with a high selectivity (about 82% or above in all cases tested), no measured production of the highly undesirable by products $CH_3Cl$, $CF_2(CH_3)_2$, or $CF_2\text{=}CHCl$. Furthermore, the conversion rates, which are all above 12%, and as high as 31.5%, are acceptable for processes of the present invention, particularly and especially for preferred processes which utilize recycle of unconverted 113 as described above. However, the amount of by-product production for the higher conversion rates is higher than is desirable for some applications.

Example 9—Gas Phase Dechlorination of $CF_2Cl$—$CFCl_2$ to CTFE with Silicon Carbide Catalyst and Propane Reducing Agent Experiments were conducted using the process as described above in general with silicon carbide catalyst, propane reducing agent and the process conditions as described in Table 9 below. The results are reported in Table 9 below:

TABLE 9

| Ex. No. | Cat. | Temp, C | CT, sec | 113: Propane Ratio | Conv. % 113 | Sel. % CTFE | By-products, mol % CF2=CFH | 123a* |
|---|---|---|---|---|---|---|---|---|
| 8A | SiC | 450 | 3 | 1:1 | 1.7 | 90.8 | | 0.2 |
| 8B | SiC | 475 | 3 | 1:1 | 2.3 | 98.1 | | 0.1 |

*123a is 1, 2-dichloro-1,1,2-trifluoroethane

As can be seen from the results reported above, processes of the present invention in which propane reducing agent is used are capable of producing reaction product with a very high selectivity (90% or above), low by-product production, and no measured production of the highly undesirable by products $CH_3Cl$, $CF_2(CH_3)_2$, or $CF_2\text{=}CHCl$. However, the conversion rates are less than is desirable for some applications, even when recycle of unconverted 113 is used as described above.

Example 10—Gas Phase Dechlorination of $CF_2Cl$—$CFCl_2$ to CTFE with TiSiC Catalyst and Propane Reducing Agent Experiments were conducted using the process as described above in general with silicon carbide catalyst, propane reducing agent and the process conditions as described in Table 10 below. The results are reported in Table 10 below:

TABLE 10

| Ex. No. | Cat. | Temp, C | CT, sec | 113: Propane Ratio | Conv., % 113 | Sel. % CTFE | By-products, mol % CF2=CFH | 123a* |
|---|---|---|---|---|---|---|---|---|
| 9A | TiSiC | 450 | 3 | 1:1 | 22.9 | 61.5 | | 8.8 |
| 9B | TiSiC | 475 | 3 | 1:1 | 35.2 | 64.1 | | 12.7 |

*123a is 1, 2-dichloro-1,1,2-trifluoroethane

As can be seen from the results reported above, processes of the present invention in which propane reducing agent is used are capable of producing reaction product with a conversion rate of 22% or above. However, the selectivity values lower than are desired for preferred applications, and by-product production are higher than are desired for preferred applications.

Example 11—Gas Phase Dechlorination of $CF_2Cl$—$CFCl_2$ to CTFE with TiSiC Catalyst and Methane Reducing Agent Experiments were conducted using the process as described above in general with TiSiC catalyst, methane reducing agent and the process conditions as described in Table 11 below. The results are reported in Table 11 below:

TABLE 11

| Ex. No. | Cat. | Temp, C | CT, sec | 113: Methane Ratio | Conv., % 113 | Sel. % CTFE | By-products, mol % CF2=CFH | CF2=CCl2 | CH3Cl |
|---|---|---|---|---|---|---|---|---|---|
| 10A | TiSiC | 500 | 3 | 1:1 | 20.4 | 96.8 | 0 | 0.7 | 0.6 |

As can be seen from the results reported above, processes of the present invention in which methane reducing agent is used are capable of producing reaction product with a conversion rate of 20.4% or above and selectivity of about 96% or above. However, the process produces $CH_3Cl$, which is an undesirable by-product for some applications.

Example 12—Extended Run of Gas Phase Dechlorination of $CF_2Cl$—$CFCl_2$ to CTFE with Hydrogen and Silicon Carbide Catalyst Experiments were conducted to test the ability of the preferred process of the present invention to maintain selectivity and conversion over the course of an extended reaction run of about six (6) hours. The process is carried out generally as described above with silicon carbide catalyst, hydrogen reducing agent in a 1:1 molar ratio, a contact time of three (3) seconds and an average reaction temperature of 525 C. A reaction product is obtained at intervals during the course of the extended run and tested for conversion, selectivity and by products, as reported in Table 12 below.

TABLE 12

| Ex. No. | Sample Interval, Hours | Conv., % 113 | Sel., % CTFE | By-products, mol % CF2=CFH | 123a* | CF2=CCl2 |
|---|---|---|---|---|---|---|
| 10A | 0.15 | 24.7 | 95.2 | 1.2 | | 0.02 |
| 10B | 3 | 19.9 | 96 | 0.78 | | 0.01 |

TABLE 12-continued

| Ex. No. | Sample Interval, Hours | Conv., % 113 | Sel., % CTFE | By-products, mol % CF$_2$=CFH | 123a* | CF$_2$=CCl$_2$ |
|---|---|---|---|---|---|---|
| 10C | 6 | 19.3 | 96 | 0.76 | | 0.01 |
| Average Conversion | | 21.3% | | | | |

*123a is 1, 2-dichloro-1,1,2-trifluoroethane

As can be seen from the results reported above, processes of the present invention which use hydrogen reducing agent and silicon carbide catalyst demonstrate unexpectedly robust performance with respect of both conversion and selectivity. In particular, the conversion was essentially the same after 3 hours of running as after 6 hours of running, and during that time the selectivity was also unchanged. In fact, even when the initial conversion (as approximated by the 0.15 hour sample) is included, the average conversion over the course of the run is 21.3%, and the change in conversion over the course of the runis low These results show an excellent, unexpected and advantageous ability of the present processes to maintain performance over the course of extended reaction periods.

Example 13—Extended Run of Gas Phase Dechlorination of CF$_2$Cl—CFCl$_2$ to CTFE with Hydrogen and Silicon Carbide Catalyst Experiments were conducted to test the ability of the preferred process of the present invention to maintain selectivity and conversion over the course of an extended reaction run of about five (5) hours. The process is carried out generally as described above with silicon carbide catalyst, hydrogen reducing agent in a 1:1 molar ratio, a contact time of five (5) seconds and an average reaction temperature of 545 C. A reaction product is obtained at intervals during the course of the extended run and tested for conversion, selectivity and by products, as reported in Table 13 below.

TABLE 13

| Ex. No. | Sample Interval, Hours | Conv., % 113 | Sel., % CTFE | By-products, mol % CF$_2$=CFH | 123a* | CF$_2$=CCl$_2$ |
|---|---|---|---|---|---|---|
| 11A | 0 | 31 | 87.8 | 2.04 | | 0.04 |
| 11B | 1 | 16.1 | 94.7 | 0.55 | | 0.03 |
| 11C | 2 | 15 | 96.5 | 0.45 | | 0.02 |
| 11D | 3 | 20.07 | 96.2 | 0.4 | | 0.01 |
| 11E | 4 | 23.5 | 95.1 | 0.64 | | 0.02 |
| 11F | 5 | 20.41 | 95.4 | 0.75 | | 0.02 |
| Average Conversion | | 21.01% | | | | |

*123a is 1, 2-dichloro-1,1,2-trifluoroethane

As can be seen from the results reported above, processes of the present invention which use hydrogen reducing agent and silicon carbide catalyst demonstrate unexpectedly robust performance with to both conversion and selectivity. In particular, the average conversion over the course of the run is 21.01%, and the change in conversion over the course of the steady state portion of the run, is low while at the same time selectively remains at 95% or above for all measurements after the initial measurement. These results show an excellent, unexpected and advantageous ability of the present processes to maintain performance over the course of extended reaction periods.

Example 14—Extended Run of Gas Phase Dechlorination of CF$_2$Cl—CFCl$_2$ to CTFE with Methane and Silicon Carbide Catalyst Experiments were conducted to test the ability of the preferred process of the present invention to maintain selectivity and conversion over the course of an extended reaction run of about five (5) hours. The process is carried out generally as described above with silicon carbide catalyst, methane reducing agent in a 1:1 molar ratio, a contact time of four (4) seconds and an average reaction temperature of 545 C. A reaction product is obtained at intervals during the course of the extended run and tested for conversion, selectivity and by products, as reported in Table 14 below.

TABLE 14

| Ex. No. | Sample Interval, Hours | Conv., % 113 | Sel., % CTFE | By-products, mol % CF$_2$=CFH | 123a* | CF$_2$=CCl$_2$ |
|---|---|---|---|---|---|---|
| 12A | 0 | 46 | 97.5 | | | 1.11 |
| 12B | 1 | 30 | 98.4 | | | 0.48 |
| 12C | 2 | 35 | 98.9 | | | 0.39 |
| 12D | 3 | 36 | 99.3 | | | 0.25 |
| 12E | 4 | 51 | 98.7 | | | 0.64 |
| 12F | 5 | 50 | 99 | | | 0.5 |
| Average Conversion | | 41.33% | | | | |

*123a is 1, 2-dichloro-1,1,2-trifluoroethane

As can be seen from the results reported above, processes of the present invention which use methane reducing agent and silicon carbide catalyst demonstrate unexpectedly robust performance with respect to both conversion and selectivity. In particular, the average conversion over the course of the run is 41.33%, and the change in conversion over the steady state portion of the run actually appears to improve. Moreover, selectively of about 97% or above is maintained for all measurements after the initial measurement. These results show an excellent, unexpected and advantageous ability of the present processes to maintain performance over the course of extended reaction periods.

Example 15—Extended Run of Gas Phase Dechlorination of CF$_2$Cl—CFCl$_2$ to CTFE without Reducing Agent and Silicon Carbide Catalyst Experiments were conducted to test the ability of the preferred process of the present invention to maintain selectivity and conversion over the course of an extended reaction run of about five (5) hours. The process is carried out generally as described above with silicon carbide catalyst, in the absence of an added reducing agent, a contact time of three (3) seconds and an average reaction temperature of 525 C. A reaction product is obtained at intervals during the course of the extended run and tested for conversion, selectivity and by products, as reported in Table 15 below.

TABLE 15

| Ex. No. | Sample Interval, Hours | Conv., % 113 | Sel., % CTFE | By-products, mol % CF$_2$=CFH | 123a* | CF$_2$=CCl2 |
|---|---|---|---|---|---|---|
| 13A | 0.15 | 7.5 | 82.3 | | | 0.02 |
| 13B | 2.5 | 2 | 99 | | | 0.02 |
| 13C | 5 | 2.4 | 99 | | | 0.02 |

TABLE 15-continued

| Ex. No. | Sample Interval, Hours | Conv., % 113 | Sel., % CTFE | By-products, mol % | | |
|---|---|---|---|---|---|---|
| | | | | $CF_2=CFH$ | 123a* | $CF_2=CCl2$ |
| Average Conversion | | 3.97% | | | | |

*123a is 1, 2-dichloro-1,1,2-trifluoroethane

Example 16—Extended Run of Gas Phase Dechlorination of $CF_2Cl$—$CFCl_2$ to CTFE without Hydrogen Reducing Agent and Nickel Packing Catalyst Experiments were conducted to test the ability of the preferred process of the present invention to maintain selectivity and conversion over the course of an extended reaction run of about six (6) hours. The process is carried out generally as described above with nickel packing catalyst in the presence of hydrogen reducing agent, a contact time of two (2) seconds and an average reaction temperature of 500 C. A reaction product is obtained at intervals during the course of the extended run and tested for conversion, selectivity and by products, as reported in Table 16 below.

TABLE 16

| Ex. No. | Sample Interval, Hours | Conv., % 113 | Sel., % CTFE | By-products, mol % | | |
|---|---|---|---|---|---|---|
| | | | | $CF_2=CFH$ | 123a* | $CF_2=CCl_2$ |
| 14A | 0.15 | 14.3 | 88.5 | 1.6 | 0.1 | |
| 14B | 3 | 4.2 | 94.7 | 0.2 | | |
| 14C | 6 | 2 | 96.9 | 0.1 | | |
| Average Conversion | | 6.83% | | | | |

*123a is 1, 2-dichloro-1,1,2-trifluoroethane

As can be seen from the results reported above, processes of the present invention which use nickel packing as catalyst and with hydrogen reducing agent do not demonstrate robust performance with respect to conversion.

Example 17—Extended Run of Gas Phase Dechlorination of $CF_2Cl$—$CFCl_2$ to CTFE with Hydrogen Reducing Agent and No Added Catalyst Experiments were conducted to test the ability of the preferred process of the present invention to maintain selectivity and conversion over the course of an extended reaction run of about five and a half (5.5) hours. The process was carried out generally as described above, using hydrogen reducing agent, a contact time of three (3) seconds and an average reaction temperature of 550 C, but without any added catalyst in the stainless steel reactor. A sample of the reaction product was obtained at intervals during the course of the extended run and tested for conversion, selectivity and by products, as reported in Table 17 below.

TABLE 17

| Ex. No. | Sample Interval, Hours | Conv., % 113 | Sel., % CTFE | By-products, mol % | | |
|---|---|---|---|---|---|---|
| | | | | $CF_2=CFH$ | 123a* | $CF_2=CCl2$ |
| 14A | 0.15 | 21.1 | 81.2 | 3.2 | 0.8 | |
| 14B | 2.5 | 16.8 | 89.3 | 1.5 | 0.3 | |

TABLE 17-continued

| Ex. No. | Sample Interval, Hours | Conv., % 113 | Sel., % CTFE | By-products, mol % | | |
|---|---|---|---|---|---|---|
| | | | | $CF_2=CFH$ | 123a* | $CF_2=CCl2$ |
| 14C | 5.5 | 15.2 | 90 | 1 | 0.5 | |
| Average Conversion | | 17.7% | | | | |

*123a is 1, 2-dichloro-1,1,2-trifluoroethane

As can be seen from the results reported above, processes of the present invention which use no catalyst and with hydrogen reducing agent do demonstrate robust performance with respect to conversion. In particular, the average conversion over the course of the run is about 18%, and the change in conversion over the course of the steady state portion of the runis low. However, the selectivity of the reaction is lower than desired for many applications and the production of by products is higher than desired for many applications.

The invention claimed is:

1. A process for the production of 1-chloro-1,2,2-trifluoroethene (CTFE) comprising reacting in the gas phase 1,1,2-trichloro-1,2,2-trifluoroethane (R-113) in the presence of a catalyst consisting essentially of a silicon-based catalyst to produce a reaction product comprising CTFE ($CF_2=CFCl$) with a CTFE selectivity of at least about 95% and a conversion of at least about 15%, wherein said reaction product is substantially free of one or more of $CH_3Cl$, $CF_2(CH_3)_2$, $CF_2=CHCl$, $F_2ClCCCl_2H$ (123a) and $CF_2=CCl_2$.

2. The process of claim 1 wherein said step of reacting in the gas phase further comprises reacting said R-113 with a reducing agent.

3. The process of claim 2 wherein said reducing agent is selected from the group consisting of an alkane, an alkene, hydrogen and combinations of two or more of these.

4. The process of claim 3 wherein said reducing agent comprises hydrogen.

5. The process of claim 3 wherein said reducing agent consists essentially of hydrogen.

6. The process of claim 3 wherein said reducing agent consists of hydrogen.

7. The process of claim 2 wherein said reducing agent is selected from the group consisting of methane, propane, hydrogen and combinations of these.

8. The process of claim 1 wherein said reaction product is substantially free of each of $CH_3Cl$, $CF_2(CH_3)_2$, $CF_2=CHCl$, $CF_2=CFH$, 123a and $CF_2=CCl_2$.

9. The process of claim 1 wherein said reacting step is a continuous process that produces a reaction product stream comprising unreacted R-113, separating at least portion of said unreacted R-113 from the reaction product stream and further comprising recycling at least a portion of said separated R-113 to said reacting step.

10. The process of claim 1 wherein said conversion is at least about 20% and said selectivity is at least about 97%.

11. A process for the production of 1-chloro-1,2,2-trifluoroethene (CTFE) comprising reacting in the gas phase 1,1,2-trichloro-1,2,2-trifluoroethane (R-113) and hydrogen in the presence of a catalyst consisting essentially of a silicon-based catalyst to produce CTFE ($CF_2=CFCl$), wherein said reacting step produces a CTFE selectivity of at least about 92% and a conversion of at least about 20%, wherein said reaction product is substantially free of one or more of $CH_3Cl$, $CF_2(CH_3)_2$, $CF_2=CHCl$, $F_2ClCCCl_2H$ (123a) and $CF_2=CCl_2$.

12. The process of claim 11 wherein said silicon-based catalyst comprises silicon carbide.

13. The process of claim 12 wherein said silicon-based catalyst consists essentially of silicon carbide.

14. The process of claim 13 wherein said silicon-based catalyst comprises one or more of silicon carbide, silicon nitride and silicon oxide.

15. A process for the production of 1-chloro-1,2,2-trifluoroethene (CTFE) comprising reacting in the gas phase 1,1,2-trichloro-1,2,2-trifluoroethane (R-113) and a reducing agent comprising one or more of methane, propane and hydrogen in the presence of a catalyst consisting essentially of a silicon-based catalyst selected from the group consisting of silicon carbide, silicon nitride and silicon oxide and combinations of two or more of these to produce CTFE ($CF_2=CFCl$), wherein said reacting step produces a reaction product that is substantially free of each of $CH_3Cl$, $CF_2(CH_3)_2$, and $CF_2=CHCl$ and which has a CTFE selectivity of at least about 96% and a conversion of at least about 25%, wherein said reaction product is substantially free of one or more of $CH_3Cl$, $CF_2(CH_3)_2$, $CF_2=CHCl$, $F_2ClCCCl_2H$ (123a) and $CF_2=CCl_2$.

16. The process of claim 15 wherein said reducing agent consists of hydrogen.

17. The process of claim 16 wherein said catalyst comprises silicon carbide.

18. The process of claim 17 wherein said catalyst comprises titanium and silicon carbide.

19. The process of claim 17 wherein said reacting step is carried out as a reaction temperature of from about 500° C. to about 600° C. and a contact time of from about 1 to about 6 seconds.

* * * * *